(12) United States Patent
Graff et al.

(10) Patent No.: US 9,308,289 B2
(45) Date of Patent: Apr. 12, 2016

(54) AIR PURIFYING LUMINAIRE

(75) Inventors: Eugene Graff, Tupelo, MS (US);
Carlton B. Plunk, Saltillo, MS (US)

(73) Assignee: Koninklijke Philips N.V., Eindhoven (NL)

( * ) Notice: Subject to any disclaimer, the term of this patent is extended or adjusted under 35 U.S.C. 154(b) by 1074 days.

(21) Appl. No.: 12/366,263

(22) Filed: Feb. 5, 2009

(65) Prior Publication Data

US 2010/0196214 A1 Aug. 5, 2010

(51) Int. Cl.
*A61L 9/20* (2006.01)
*F24F 3/16* (2006.01)
*F24F 13/078* (2006.01)
*F24F 7/00* (2006.01)

(52) U.S. Cl.
CPC ............. *A61L 9/20* (2013.01); *F24F 3/1603* (2013.01); *F24F 13/078* (2013.01); *A61L 2209/12* (2013.01); *F24F 2003/1667* (2013.01); *F24F 2007/004* (2013.01)

(58) Field of Classification Search
CPC ........................................................ A61L 9/20
USPC .............................. 422/120, 121; 250/455.11
See application file for complete search history.

(56) References Cited

U.S. PATENT DOCUMENTS

| | | | |
|---|---|---|---|
| 2,350,462 A * | 6/1944 | Johns ............................. | 362/216 |
| 2,359,021 A | 9/1944 | Campbell | |
| 2,654,021 A * | 9/1953 | Bartholomew ............... | 362/228 |
| 3,326,112 A | 6/1967 | Sadlow | |
| 3,370,502 A | 2/1968 | Wilks | |
| 3,541,504 A | 11/1970 | Bush | |
| 3,576,593 A * | 4/1971 | Cicirello ............................ | 422/4 |
| 3,766,397 A * | 10/1973 | Rockson ................... | 250/432 R |
| 3,869,614 A | 3/1975 | Munk | |
| 3,937,967 A * | 2/1976 | Steinitz ......................... | 250/435 |
| 3,948,772 A | 4/1976 | Ellner | |
| 3,984,726 A | 10/1976 | Ramler | |
| 4,201,916 A | 5/1980 | Ellner | |
| 4,204,956 A | 5/1980 | Flatow | |
| 4,246,101 A | 1/1981 | Selby | |
| 4,272,679 A | 6/1981 | Blades | |
| 4,279,254 A | 7/1981 | Boschetti | |
| 4,403,826 A | 9/1983 | Presby | |
| 4,424,449 A | 1/1984 | O'Brill | |
| 4,504,114 A | 3/1985 | Arrington | |
| 4,529,912 A | 7/1985 | Northrup | |
| 4,578,583 A | 3/1986 | Ciammaichella | |
| 4,665,627 A | 5/1987 | Wilde | |
| 4,742,231 A | 5/1988 | Bridgen | |
| 4,801,375 A | 1/1989 | Padilla | |
| 4,885,471 A | 12/1989 | Telfair | |
| 4,904,876 A | 2/1990 | Nobbs | |
| 4,968,437 A | 11/1990 | Noll | |
| 4,975,584 A | 12/1990 | Benjamin | |
| 5,026,996 A | 6/1991 | Fricke | |
| 5,106,512 A | 4/1992 | Reidy | |
| 5,203,989 A | 4/1993 | Reidy | |
| RE34,513 E | 1/1994 | Ellner | |
| 5,311,101 A | 5/1994 | Noriki | |

(Continued)

*Primary Examiner* — Sean E Conley

(57) ABSTRACT

A luminaire system having a lamp compartment and sterilization compartment permitting both illumination and the sterilizing of airborne bacteria. The sterilization compartment has one or more germicidal lamps to sterilize airborne bacteria when air is circulated through the luminaire system. The lamp compartment has one or more lamps to illuminate the desired outside environment away from the system.

20 Claims, 4 Drawing Sheets

(56) References Cited

U.S. PATENT DOCUMENTS

| | | | | |
|---|---|---|---|---|
| 5,340,974 | A | 8/1994 | Zalewski | |
| 5,401,394 | A | 3/1995 | Markham | |
| 5,484,538 | A | 1/1996 | Woodward | |
| 5,521,392 | A | 5/1996 | Kennedy | |
| 5,545,335 | A | 8/1996 | Sween | |
| 5,628,895 | A | 5/1997 | Zucholl | |
| 5,660,719 | A | 8/1997 | Kurtz | |
| 5,785,845 | A | 7/1998 | Colaiano | |
| 5,883,711 | A | 3/1999 | Haverlag | |
| 5,891,399 | A | 4/1999 | Owesen | |
| 5,922,605 | A | 7/1999 | Feurstein | |
| 5,997,397 | A | 12/1999 | Frickel | |
| 6,028,396 | A | 2/2000 | Morrissey | |
| 6,042,720 | A | 3/2000 | Reber | |
| 6,110,424 | A | 8/2000 | Maiden | |
| 6,123,434 | A * | 9/2000 | Meltzer | 362/260 |
| 6,144,035 | A | 11/2000 | Piper | |
| 6,180,003 | B1 | 1/2001 | Reber | |
| 6,193,603 | B1 | 2/2001 | Tai | |
| 6,264,836 | B1 | 7/2001 | Lantis | |
| 6,312,589 | B1 | 11/2001 | Jarocki | |
| 6,362,573 | B1 | 3/2002 | Helbing | |
| 6,522,086 | B2 | 2/2003 | Gemunder | |
| 6,551,493 | B2 | 4/2003 | Mori | |
| 6,567,158 | B1 | 5/2003 | Falciai | |
| 6,569,319 | B2 | 5/2003 | Kuennen | |
| 6,579,495 | B1 | 6/2003 | Maiden | |
| 6,589,486 | B1 | 7/2003 | Spanton | |
| 6,603,126 | B2 | 8/2003 | Yamada | |
| 6,693,530 | B1 | 2/2004 | Dowens | |
| 8,080,203 | B2 * | 12/2011 | First et al. | 422/24 |
| 2001/0027926 | A1 | 10/2001 | Mori | |
| 2002/0014864 | A1 | 2/2002 | Gemunder | |
| 2002/0047546 | A1 | 4/2002 | Kayser | |
| 2002/0057570 | A1 * | 5/2002 | Schaareman | 362/296 |
| 2002/0085947 | A1 | 7/2002 | Deal | |
| 2002/0098127 | A1 | 7/2002 | Bollini | |
| 2002/0155805 | A1 | 10/2002 | Paschke | |
| 2002/0171368 | A1 | 11/2002 | Little | |
| 2003/0003028 | A1 | 1/2003 | Tomaselli | |
| 2003/0075490 | A1 | 4/2003 | Lifschitz | |
| 2003/0099569 | A1 | 5/2003 | Lentz | |
| 2003/0213755 | A1 | 11/2003 | Hanbli | |
| 2003/0217641 | A1 | 11/2003 | Palestro | |

\* cited by examiner

AIR PURIFYING LUMINAIRE

TECHNICAL FIELD

The present invention relates to a luminaire system and particularly to a luminaire system utilizing air purification.

DETAILED DESCRIPTION

Figure 1:
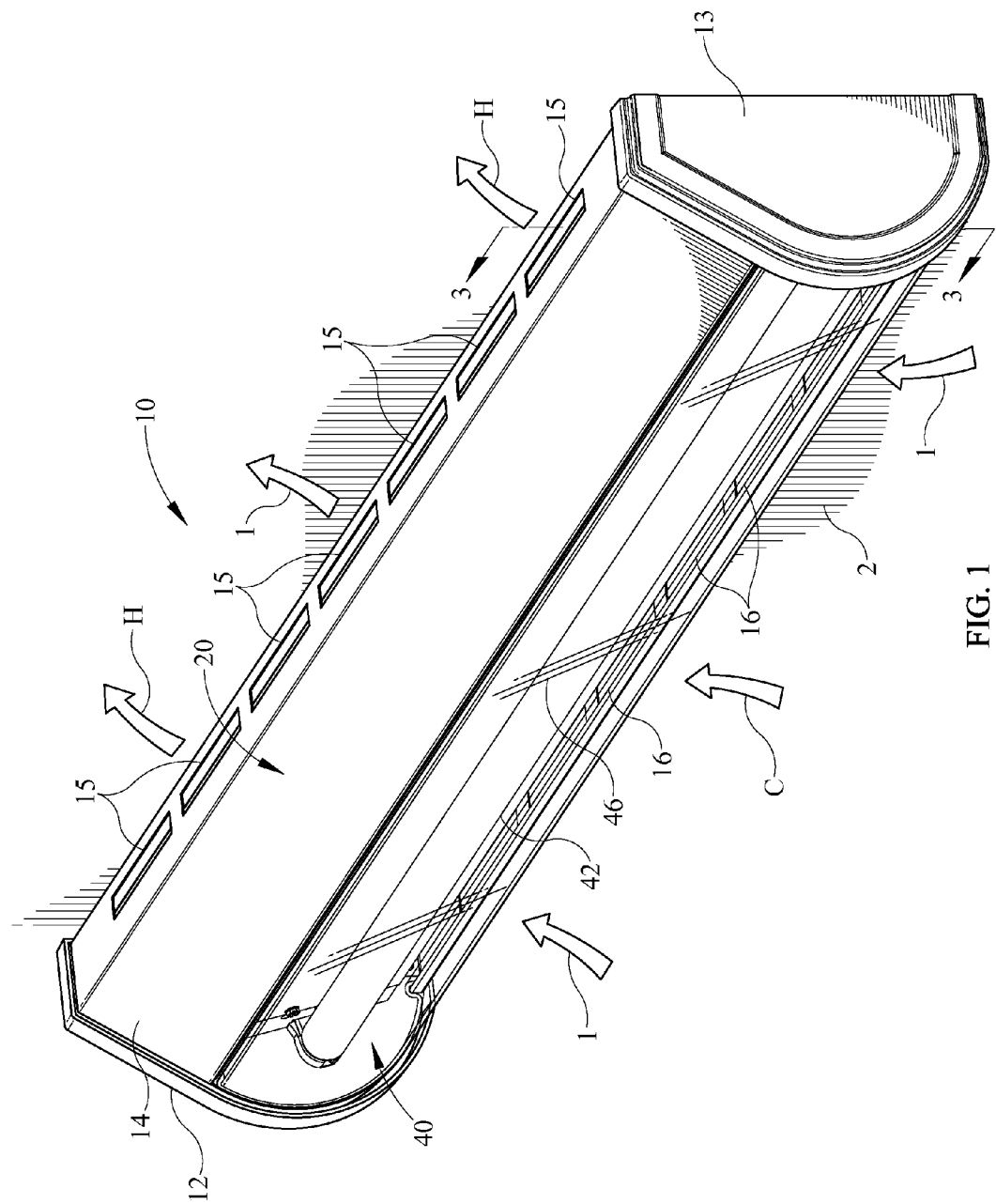
FIG. 1 is a perspective top view of an embodiment of a luminaire system.

A luminaire system 10 has an enclosed sterilization compartment 20 for destroying airborne bacteria and a lamp compartment 40 for illuminating the desired outside environment away from the system. According to one embodiment, air 1 is circulated through the sterilization compartment where it is irradiated with ultraviolet light, and then exits from the system. The exposure time and distance from the ultraviolet lamp dictates the effectiveness of the killing of bacteria.

As shown in FIGS. 1-4, the elongated luminaire system 10 secured against wall 2 has a pair of end caps 12 and 13 with lamp compartment 40 positioned below the sterilization compartment 20. Lamp compartment 40 has a lamp 42 positioned with a reflector 44 to illuminate through a lens 46 to the desired area away from the system 10. Lamp compartment 40 may be provided in a variety of quantities, sizes, and locations within the system 10 and may contain a variety of lamps such as but not limited to fluorescent, CFLs, LEDs, and incandescent to indirectly or directly illuminate from luminaire system 10 in a variety of applications. Sterilization compartment 20 conceals an ultraviolet lamp 22 within the system 10, providing ultraviolet light within the compartment. Sterilization compartment 20 may also be provided in a variety of quantities, sizes, locations, and shapes within the system 10 and may contain a variety of ultraviolet emitting lamps or the like and still sterilize the air flow though the system 10. Sterilization compartment 20 may contain baffles 24 and 26 to minimize ultraviolet light from leaking from the sterilization compartment, for instance into lamp compartment 40 or out of the system 10. An exit baffle 26 may be positioned above ultraviolet lamp 22 and an inlet baffle 24 is positioned below the ultraviolet lamp. The possibility of ultraviolet light escaping can be further reduced by applying an absorptive coating or painting to the interior surfaces of the baffles and the other interior surfaces of the sterilization compartment. The shapes and position of the baffles or interior surfaces of the luminaire may provide a variety of air flow properties and pathways within the sterilization compartment or the system, such as to vary the exposure time and effectiveness of the ultraviolet lamps, when air is circulated through the luminaire to be sterilized. A cut-off switch (not shown) may also be used to prevent the ultraviolet light from escaping the luminaire. For instance, the cut-off switch may be located in sterilization compartment 20 whereby the ultraviolet lamp 22 is made inoperable when a portion of the housing wall 14 is opened to gain access to the ultraviolet lamp.

As shown in FIGS. 1-4, luminaire system 10 has a throughway 30 permitting natural convection to circulate air 1 through the system. The phenomenon known as "natural or cooling convection" is also referred to as "natural ventilation". The natural convection is a result of a temperature difference created within a system in which heating itself may cause the fluid motion of air, via expansion and buoyancy force, while permitting heat to be transported by this motion of air. Thus, warm air will rise and exit the system through an opening, being replaced with cooler air from outside the system. The luminaire system 10 with natural convection may be utilized in a variety of applications in use such as but is not limited to the wall mounted fixture as shown in FIGS. 1-4, recessed lighting, track lighting, or lighting applications for ambient, accent, task, or decorative lighting.

Figure 2:
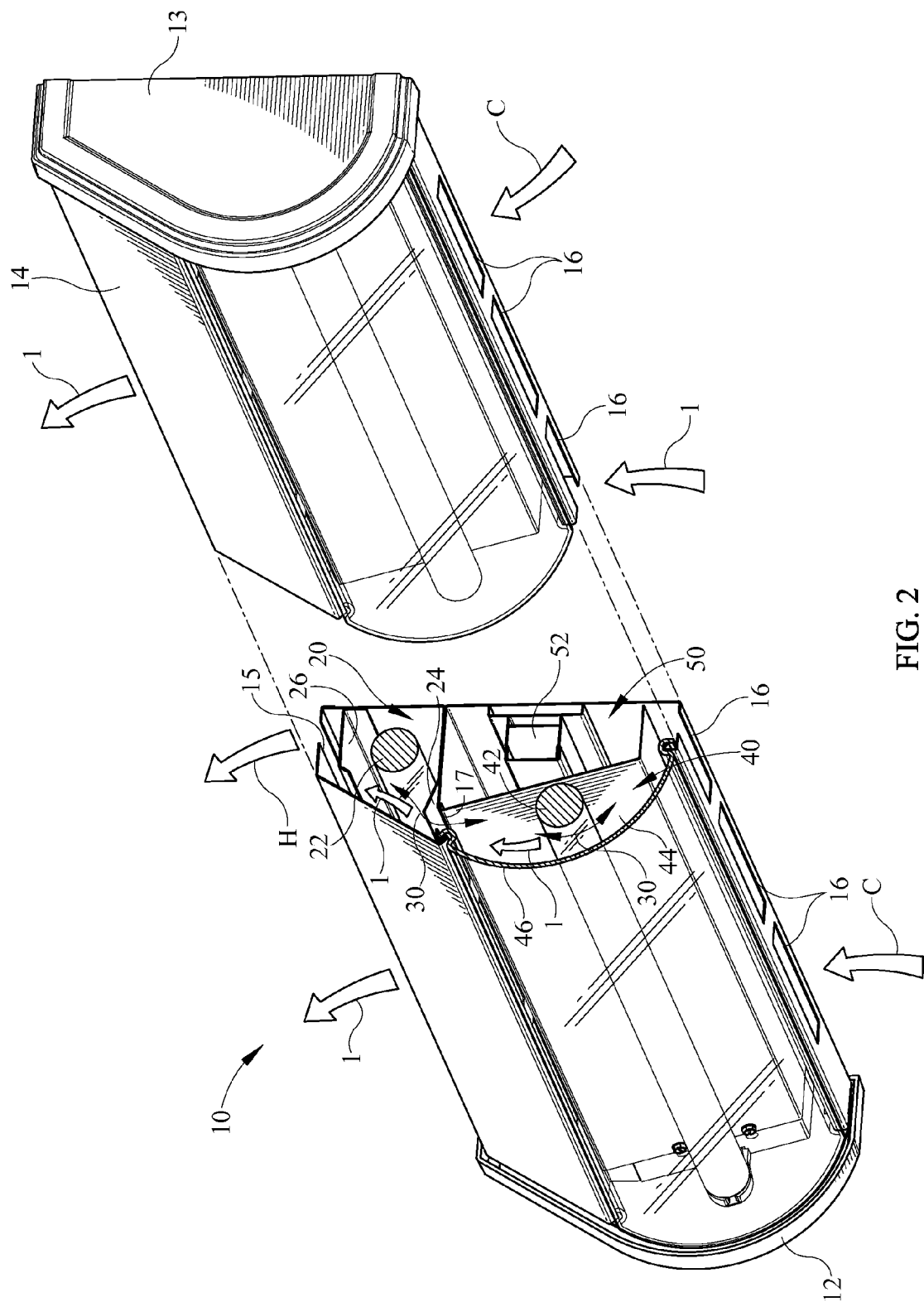
FIG. 2 is a perspective bottom view of the luminaire system of FIG. 1 with the housing partially broken away illustrating the interior of the luminaire.
Figure 3:
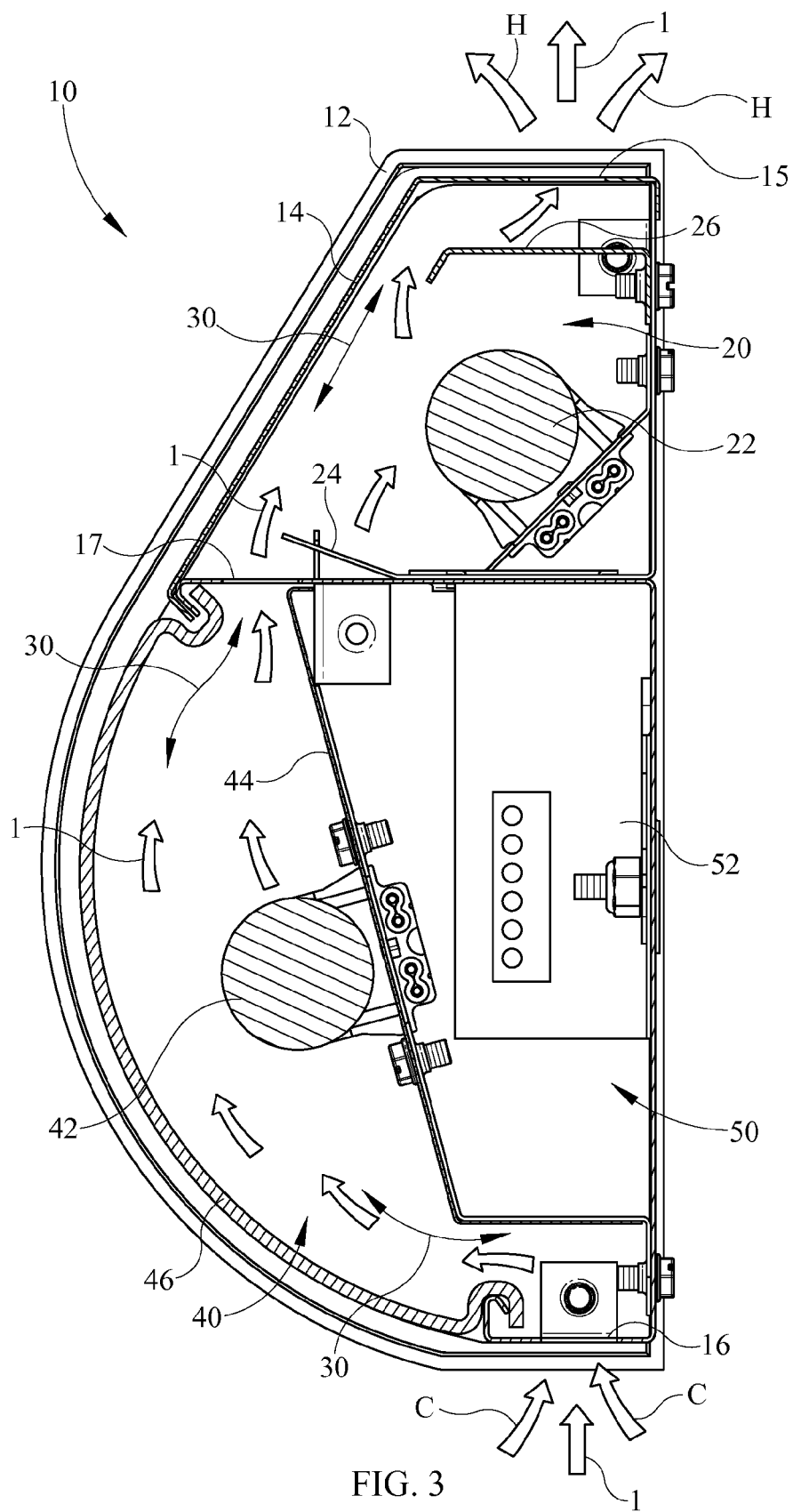
FIG. 3 is an enlarged sectional view of the luminaire system of FIG. 1 taken along line 3-3.
Figure 4:
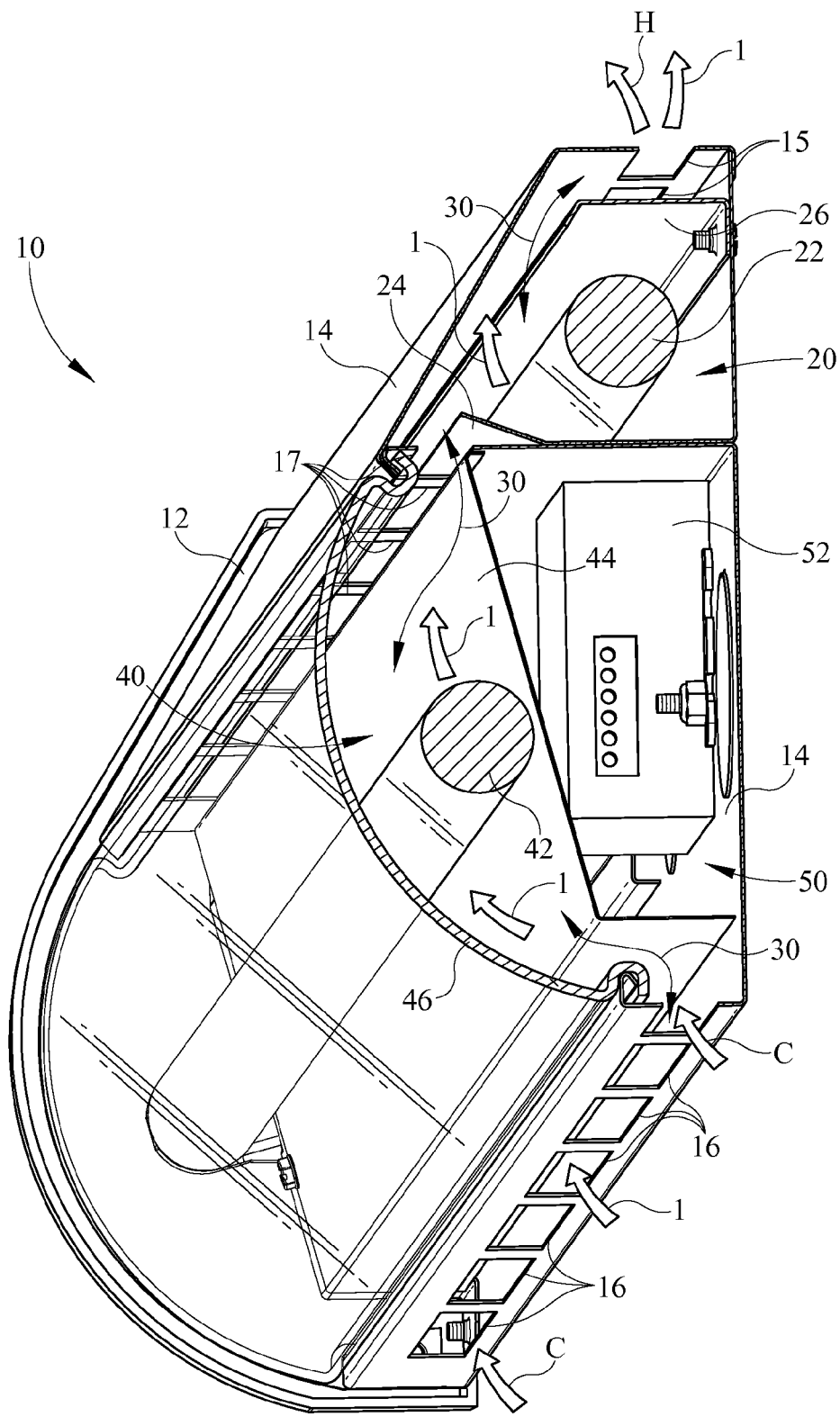
FIG. 4 is a perspective bottom view of the sectional view of the luminaire system of FIG. 3.

As shown in FIGS. 1-4, the luminaire system 10 has an elongated throughway 30, path, or flue. Luminaire housing wall 14 has one or more outlet apertures 15 disposed above one or more inlet apertures 16, thus openings 15 and 16 are at different elevations within the luminaire. Outlet apertures 15 and inlet apertures 16 are shown in the upper end and lower end of the luminaire system 10, respectively. Throughway 30 runs from inlet apertures 16 adjacent the bottom end of luminaire system 10 up to outlet apertures 15 adjacent the upper end of system 10. Outlet apertures 15 and inlet apertures 16 are interconnected by at least one continuous throughway 30 that passes through sterilization compartment 20 allowing the flow of air to be sterilized by the ultraviolet radiation emitted from ultraviolet lamp 22. Because of the natural convection, inlet apertures 16 permit cooler air, shown as C, from outside the luminaire system 10 to enter, while the outlet apertures 15 permit the heated and sterilized air, shown as H, to exit the system. As shown in FIGS. 2-4, throughway 30 may also pass through lamp compartment 40 wherein one or more interconnecting apertures 17 or slots permit air flow 1 between lamp compartment 40 and sterilization compartment 20. As a result, throughway 30 can be defined by a variety of walls of the system or housing walls 14 as shown in FIGS. 1-4. For instance, but not limited to, throughway 30 may extend through both lamp and sterilization compartments as shown in the figures or be a separately formed throughway only allowing air to pass by the ultraviolet lamp.

Although throughway 30 and apertures 15 and 16 are shown in detail in the FIGS. 1-4, it is merely representative of one embodiment of the invention. There are a variety of different quantities, shapes, construction, orientation, and dimensions of the apertures 15 and 16 and throughway 30 that may be used as will be understood by those skilled in the art, and still permit air to circulate through the system to be sterilized. For example, by varying the length or position of the throughway and the size of the apertures one skilled in the art can make the natural convection more conducive to a particular use of a specific luminaire system.

Convection air currents as a result of heat from at least the operation of the ultraviolet lamp 22 causes air to be circulated through the sterilization chamber 20. Inlet apertures 16 act to draft in air 1 from the surrounding outside environment through throughway 30, removing heat generated from one or more ultraviolet lamps 22 within the throughway. The air 1 then exits from outlet apertures 15. Alternatively, as described above, lamp 42 of lamp compartment 40 as shown in FIGS. 2-4 may also be located in the throughway 30 and may also heat the air within the throughway when in operation. Conducted heat thus warms air 1 within throughway 30 adjacent each lamp, creating a warm air environment within the throughway. This heated air H will draft up through throughway 30 and exit out of the outlet apertures 15, whereby cooler air C will be drafted through the inlet apertures 16 and replace the exiting heated air within the throughway. This continuous circulation of air 1 caused by the natural convection permits ultraviolet lamps 22 to sterilize the airborne bacteria while increasing the natural cooling of the electrical components of the system. The air 1 is circulated without the use of mechanical devices, such as fans or the like, however such mechanical devices may also be used to either assist in the natural convection or to circulate by forced air alone.

Electrical components may be separate and external to the throughway 30 and circulating air 1 thereby allowing the air to pass through the system without contact with the electrical components. As shown in FIGS. 2-4, lamp 42 is positioned internally to throughway 30 although the lamp may be positioned external to the air flow and still contribute heat thereto. An electrical compartment 50 may contain electrical components such as but not limited to a driver 52 or ballast and may be positioned external to throughway 30 as shown in FIGS. 2-4. One or more drivers 52 or ballasts may be used to operate lamp 42 or ultraviolet lamp 22. Any housing or compartment containing such electrical components that generate heat as for example circuits, lamps, sensors, drivers, or the like, may alternatively be positioned within the throughway and thereby cooled by the air circulation. As shown in FIGS. 2-4, electrical compartment 50 is separate and isolated from throughway 30. Any electrical component that reacts poorly to increased temperature, moisture, and dust may be positioned externally from throughway 30 and still utilize the natural convection. Also, compartments external to throughway 30 may be permanently sealed. For instance, a permanent seal can be provided to isolate the electrical compartment 50 or alternatively to isolate the lamp compartment. Any electrical components that are sealed and not located in throughway 30 will not be subjected to dust, moisture, etc., that can arise from circulating air 1 from the outside environment. Dust and moisture may also damage other components of the luminaire such as by building up on the interior of lens 46 reducing light output of the luminaire system.

Although electrical components may be separate from throughway 30, structure may be provided to thermally conduct heat into the throughway in order to dissipate heat generated while in use, or to aid in the natural convection process occurring in throughway 30. As shown in FIGS. 2-4, the electrical compartment 50 may lie adjacent to throughway 30 and may conductively radiate heat through a portion of the lamp compartment wall or sterilization wall. Portions of the housing walls 14 surrounding throughway 30 may be constructed so as to be conducive to heat conduction from the electrical components. Electrical compartment 50, as shown in FIGS. 2-4, and other electrical component housings, such as lamp compartment 40, may be external to throughway 30 and thermally interconnected to the throughway 30 by a heat sink wall (not shown) or other conductive material. A heat sink wall will increase in temperature during operation of the components within the compartment and thereby conduct heat into throughway 30. A heat sink wall may also include at least one fin projecting into throughway 30 to achieve a more efficient heat transfer to air 1 inside the throughway. The heat sink walls may be a variety of different constructions, quantities, shapes, and in various locations within the system and still be used to conduct heat generated by any heat generating components into the throughway of the system.

As discussed above, the natural convection within throughway 30 can be used to remove heat generated from lamps 22 and 42 and other various electrical components, such as the ballast or driver 52. One resultant advantage is a decrease in temperature within the interior of compartments such as lamp compartment 40, sterilization compartment 20, and other electrical component housings, such as the electrical compartment 50, thereby increasing the life expectancy of lamps 22 and 42 or other electrical components. The decreased temperature surrounding lamps 22 and 42 can also act to increase the light output of each lamp.

It is to be understood that the heat generated while either or both of the ultraviolet lamp 22 or lamp 42 are in operation may be introduced within throughway 30 at respective ends of the throughway or alternatively be positioned at a variety of lengths thereof. It is also to be understood to those skilled in the art that throughway 30 may be provided in a variety of positions, cross-sections, and thermal properties contributing to the efficiency of the natural convection. Inlet and outlet apertures 16 and 15 of the throughway 30 may also be a variety of sizes, locations, and shapes contributing to the natural convection.

Although, luminaire system 10 with lamp compartment 40 and sterilization compartment 20 are illustrated in detail in FIGS. 1-4, it is merely generally representative of such a system, and it should be understood that there are many variations of luminaire system that may be used with the germicidal feature of the embodiments herein described to permit the sterilization of airborne bacteria in air circulated within the system when in use to illuminate the outside environment away from the luminaire.

It is to be understood that while certain embodiments of the invention have been illustrated and described, it is not limited thereto except insofar as such limitations are included in the following claims and allowable functional equivalents thereof.

We claim:

1. An air purifying luminaire comprising:
    a light fixture having a first compartment adjacent a second compartment, said first compartment containing one or more germicidal lamps concealed in said first compartment for emitting ultraviolet light, and said second compartment containing one or more lamps illuminating a desired area away from said light fixture; and
    a fixture inlet spaced from and in flow communication with a fixture outlet thereby forming a throughway passing adjacent said one or more germicidal lamps, whereby a cooling convection flow of air enters said light fixture through said fixture inlet and passes said one or more germicidal lamps concealed in said light fixture and exits said light fixture through said fixture outlet when said one or more germicidal lamps is in operation, thereby sterilizing said convection flow of air, wherein the one or more lamps illuminating the desired area is not a germicidal lamp, wherein said first compartment includes one or more baffles including a first baffle defining a wall located inside said first compartment, between said one or more germicidal lamps and the fixture outlet and separated from the fixture outlet, and extending in a direction of a length of said one or more germicidal lamps for sufficiently reducing the ultraviolet light emitted from said one or more germicidal lamps from leaking outwardly away from the fixture outlet, wherein the one or more baffles include absorptive coating on interior surfaces of the one or more baffles for absorbing the ultraviolet light, wherein the interior surfaces are located on sides of the one or more baffles facing the one or more germicidal lamps.

2. The air purifying luminaire as in claim 1 wherein said first compartment is positioned upwardly from said second compartment.

3. The air purifying luminaire as in claim 1 wherein said light fixture has a lower end and an upper end, wherein said fixture inlet is adjacent said lower end of said light fixture and said fixture outlet is adjacent said upper end of said light fixture.

4. The air purifying luminaire as in claim 1 wherein said throughway passes through said second compartment.

5. The air purifying luminaire as in claim 1 further includes one or more slots interconnecting said first compartment and said second compartment.

6. The air purifying luminaire as in claim 1 wherein said convection flow of air circulates passively without fans through said fixture when said one or more lamps of said second compartment is in operation as a result of a temperature difference between exterior and interior of the air purifying luminaire.

7. A luminaire system for air purification comprising:
a luminaire fixture having a lamp compartment and a germicidal lamp compartment, said germicidal lamp compartment containing one or more germicidal lamps;
said germicidal lamp compartment having one or more air inlet apertures connected by a throughway to one or more air outlet apertures, whereby air travels into said one or more air inlet apertures through said throughway and exits out of said germicidal lamp compartment through said one or more air outlet apertures;
said one or more germicidal lamps of said germicidal lamp compartment being configured to emit ultraviolet light into said throughway within said luminaire fixture; and
one or more illuminating lamps of said lamp compartment being configured to emit illuminating light away from said luminaire fixture to a desired outside environment, wherein the one or more illuminating lamps is not a germicidal lamp,
wherein said germicidal lamp compartment includes one or more baffles defining a wall located inside said germicidal lamp compartment, between said one or more germicidal lamps and the one or more air outlet apertures and separated from the one or more air outlet apertures, and extending in a direction of a length of said one or more germicidal lamps for sufficiently reducing the ultraviolet light emitted from said one or more germicidal lamps from leaking outwardly away from said luminaire system, wherein the one or more baffles include absorptive coating on interior surfaces of the one or more baffles for absorbing the ultraviolet light, wherein the interior surfaces are located on sides of the one or more baffles facing the one or more germicidal lamps.

8. The luminaire system as in claim 7 wherein said air travels passively without fans by a cooling convection within said luminaire fixture as a result of a temperature difference between exterior and interior of the luminaire system.

9. The luminaire system as in claim 7 wherein said one or more germicidal lamp compartment is positioned substantially above said lamp compartment.

10. The luminaire system as in claim 7 wherein said lamp compartment includes a lens.

11. The luminaire system as in claim 7 wherein said throughway passes through said lamp compartment.

12. The luminaire system as in claim 7 further including a plurality of electronics in electrical communication with said one or more germicidal lamps of said germicidal lamp compartment or said one or more lamps of said lamp compartment, wherein the plurality of electronics are external to the throughway for allowing the air to pass through the throughway without contact with the plurality of electronics.

13. A luminaire system comprising:
a lamp compartment in flow communication with a sterilization compartment, wherein said sterilization compartment includes one or more ultraviolet lamps for emitting ultraviolet light, and said lamp compartment having one or more illuminating lamps illuminating a desired area away from said luminaire system; and
a system inlet in fluid communication with a system outlet thereby forming a throughway extending through said sterilization compartment and said lamp compartment, wherein a cooling convection flow of air enters into said system inlet and passes adjacent said one or more ultraviolet lamps of said sterilization compartment whereby said air is sterilized, and said sterilized air exits said luminaire system through said system outlet, wherein the one or more illuminating lamps is not a germicidal lamp,
wherein said sterilization compartment includes one or more baffles defining a wall located inside said sterilization compartment, between said one or more ultraviolet lamps and the system outlet and separated from the system outlet, and extending in a direction of a length of said one or more ultraviolet lamps for sufficiently reducing the ultraviolet light emitted from said one or more ultraviolet lamps from leaking outwardly away from said luminaire system, wherein the one or more baffles include absorptive coating on interior surfaces of the one or more baffles for absorbing the ultraviolet light, wherein the interior surfaces are located on sides of the one or more baffles facing the one or more ultraviolet lamps.

14. The luminaire system as in claim 13 wherein said one or more ultraviolet lamps are concealed within said sterilization compartment and emit ultraviolet light and the illuminating lamps emit visible light.

15. The luminaire system as in claim 13 wherein each of said system inlet and said system outlet includes one or more slots.

16. The luminaire system as in claim 13 wherein said system inlet is proximate a lower end of said system and said system outlet is proximate an upper end of said system.

17. The luminaire system as in claim 13, wherein the luminaire system is a wall mounted light fixture.

18. The luminaire system as in claim 13 wherein said throughway is defined by one or more apertures interconnecting said lamp compartment with said sterilization compartment.

19. The luminaire system as in claim 13 wherein said sterilization compartment is located substantially above said lamp compartment.

20. The air purifying luminaire of claim 1, wherein a second baffle of the one or more baffles defines a further wall extending in the direction of the length of said one or more germicidal lamps, the further wall being located opposite the wall between said one or more germicidal lamps and the fixture outlet, the further wall being configured to reduce exit of the ultraviolet light from the first compartment to the second compartment through slots interconnecting the first compartment and the second compartment, and wherein the wall and the further wall have different shapes.

\* \* \* \* \*